(12) United States Patent
Zerrer et al.

(10) Patent No.: US 6,391,962 B2
(45) Date of Patent: May 21, 2002

(54) COPOLYMERS AND THEIR USE AS DRIFT CONTROL AGENTS

(75) Inventors: Ralf Zerrer, Karlstein; Rainer Kupfer, Hattersheim, both of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/784,536

(22) Filed: Feb. 15, 2001

(30) Foreign Application Priority Data

Feb. 16, 2000 (DE) ......................... 100 07 044

(51) Int. Cl.$^7$ ..................... C08K 5/00; A01N 25/00
(52) U.S. Cl. ..................... 524/547; 424/405
(58) Field of Search .............. 524/547; 424/405, 424/409

(56) References Cited

U.S. PATENT DOCUMENTS

| | | | |
|---|---|---|---|
| 4,413,087 A | 11/1983 | Bernot | |
| 4,505,827 A | 3/1985 | Rose et al. | |
| 5,847,096 A | 12/1998 | Schubert et al. | |
| 6,218,492 B1 | 4/2001 | Hill et al. | 526/287 |
| 6,335,357 B1 * | 1/2002 | Okui | 514/404 |

FOREIGN PATENT DOCUMENTS

| | | |
|---|---|---|
| DE | 25 49 840 | 5/1977 |
| DE | 197 52 093 | 7/1999 |
| EP | 0 852 238 | 7/1998 |
| GB | 148 22 52 | 8/1977 |
| WO | WO 99/26991 | 6/1999 |

OTHER PUBLICATIONS

PCT Search Report.
Abstract of WO 99/26991.
European Search Report.
Daniel L. Comins and A.H. Abdullah; Regioselective Addition of Grignard Reagents to 1–Acylpyridinium Salts. A convenient Method for the Synthesis of 4–Alkyl (aryl) pyridines, American Chemical Society, pp. 4315–4319, 1982.
U.S. application No. 09/196,668.

* cited by examiner

*Primary Examiner*—Christopher Henderson
(74) *Attorney, Agent, or Firm*—Richard P. Silverman

(57) ABSTRACT

What is claimed are copolymers consisting essentially of from 1 to 90% by weight of the repetitive structural unit of the formula (1)

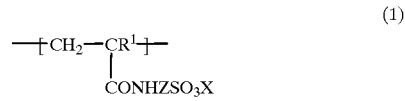

in which $R^1$ is hydrogen or methyl, Z is a $C_1$–$C_4$-alkylene group and X is hydrogen, an alkali metal or ammonium, from 10 to 99% by weight of a repetitive structural unit which is derived from olefinically unsaturated comonomers containing at least one oxygen, nitrogen, sulfur or phosphorus atom and from 0 to 20% by weight of crosslinking structures originating from monomers having at least two olefinic double bonds.

These copolymers are suitable for use as drift control agents for crop protection compositions.

1 Claim, No Drawings

COPOLYMERS AND THEIR USE AS DRIFT CONTROL AGENTS

BACKGROUND OF THE INVENTION

The present invention relates to the use of water-soluble or water-swellable copolymers based on acrylamidoalkylsulfonic acid salts as drift control agents in crop protection compositions.

Pesticides are applied in a highly efficient manner to agricultural production fields using spray tanks in airplanes, tractors and other devices. To achieve an application of the active substances which is as accurate as possible, it is necessary to obtain a spray cone which is as narrow as possible, and to avoid a drift of the spray mist from the target area.

The drift of the spray cone is determined substantially by the droplet size. The smaller the droplets, the longer the residence time in the air and the higher the tendency to evaporate and/or to drift horizontally and to miss the target location. The drift effect can be reduced considerably by adding suitable drift control agents to pesticide formulations, which drift control agents increase the size of the droplets in the spray mist. The formulations modified by drift control agents additionally have to be insensitive to shear forces to which they are exposed in the spray pumps and nozzles. Drift control agents are furthermore required to have good biological degradability, compatibility with the other components of the crop protection composition and high storage and temperature stability. It is well known in the prior art that the rheological properties of aqueous compositions can be modified by adding water-soluble polymers, for example polyacrylamides, acrylamide/acrylic acid polymers, sodium polyacrylate, carboxymethylcellulose, hydroxyethylcellulose, methylcellulose, polysaccharides and natural and synthetic guar gum (U.S. Pat. Nos. 4,413,087, 4,505,827, 5,874,096).

Unsatisfactory is the viscoelastic behavior of the additives when shear and pressure forces are applied.

Under mechanical stress in the spraying device, the viscosity is lowered and the droplet size in the spray mist is reduced.

It is a further disadvantage that the polymers used for modifying the viscosity of the aqueous preparations lose some of their thickening action in the presence of electrolytes, for example sodium chloride, calcium chloride and magnesium sulfate. Cellulose derivatives are highly electrolyte-tolerant but not temperature-stable enough. Biopolymers, such as xanthan gum, are electrolyte- and thermostable, but expensive and poorly storage-stable.

Both for economical and ecological reasons, there are attempts to find suitable drift control agents which effectively increase the droplet volumes of the aqueous compositions, even under the influence of shear forces, in the presence of electrolytes and under thermal stress, and which reduce the drift of the spray cone.

Polymers of acrylamido-2-methyl-propanesulfonic acid and acrylamide and their use as additives in cement slurries for cementing deep underground drillings are known from DE 197 52 093.

SUMMARY OF THE INVENTION

Surprisingly, it has been found that water-soluble and water-swellable copolymers based on acrylamidoalkylsulfonates and olefinically unsaturated monomers containing at least one oxygen, nitrogen, sulfur or phosphorus atom and from 0 to 20% by weight of a suitable crosslinker are very good thickeners for aqueous preparations and, when these compositions are sprayed, effect an increase in the particle size and a reduction of the spray cone. In addition, the polymers used according to the invention have good viscosity properties. Under the action of shear forces, the particle volumes are reduced only slightly. In addition, the compositions according to the invention have high electrolyte, temperature and storage stability.

DESCRIPTION OF THE PREFERRED EMBODIMENTS

The invention provides copolymers consisting essentially of from 1 to 90% by weight of the repetitive structural unit of the formula (1)

$$-[CH_2-CR^1]-\\ \phantom{xxxxx}|\\ \phantom{xxxxx}CONHZSO_3X \tag{1}$$

in which $R^1$ is hydrogen or methyl, Z is a $C_1$–$C_4$-alkylene group and X is hydrogen, an alkali metal or ammonium, from 10 to 99% by weight of a repetitive structural unit which is derived from olefinically unsaturated comonomers containing at least one oxygen, nitrogen, sulfur or phosphorus atom and from 0 to 20% by weight of crosslinking structures originating from monomers having at least two olefinic double bonds.

The exceptions are those copolymers consisting of 1–99% by weight of structural units of the formula (2)

$$\begin{array}{c} R^2 \\ | \\ -[CH_2-C]- \\ | \\ O=C-N-R^3-SO_3X \\ | \\ R^4 \end{array} \tag{2}$$

where $R^2$=hydrogen or methyl, $R^3$=$C_1$–$C_{22}$-alkylene, $R^4$=$C_1$–$C_{22}$-alkyl or hydrogen and X=ammonium, lithium, sodium, potassium, an amine or a mixture of these substances and 99–1% by weight of structural units of the formula (3)

$$\begin{array}{c} R^5 \\ | \\ -[CH_2-C]- \\ | \\ C=O \\ | \\ N \\ R^6 \diagup \diagdown R^7 \end{array} \tag{3}$$

where $R^5$=hydrogen or methyl, $R^6$ and $R^7$ independently of one another are hydrogen or $C_2$–$C_{22}$-alkyl.

The preferred monomer of the formula (1) is 2-acrylamido-2-methylpropanesulfonic acid and its salts, preferably the ammonium salt. Suitable olefinically unsaturated monomers containing at least one oxygen, nitrogen, sulfur or phosphorus atom are, for example, styrenesulfonic acid, acrylamidopropylmethylenesulfonic acid (AMPS), vinylsulfonic acid, vinylphosphonic acid, allylsulfonic acid, methallylsulfonic acid, acrylic acid, methacrylic acid and maleic acid (and its anhydride) and the salts of the acids mentioned above with mono- and divalent counterions. Preferred counterions are lithium, sodium, potassium, magnesium, calcium, ammonium, monoalkylammonium, dialkylammonium, trialkylammonium or tetraalkylammonium, where the alkyl substituents of the amines independently of one another are $C_1$–$C_{22}$-alkyl radicals which may be substituted by 0 to 3 hydroxyalkyl groups, the alkyl chain length of which may vary in a range from $C_2$–$C_{10}$. Additionally, it is also possible to use mono- to triethoxylated ammonium compounds with a different degree of ethoxylation. Particularly preferred counterions are sodium and ammonium. The degree of neutralization of the mole fraction of the acids described above may also differ from 100%. Suitable are all degrees of neutralization between 0 and 100%, the range between 70 and 100% being particularly preferred.

Furthermore suitable are esters of acrylic or methacrylic acid with aliphatic, aromatic or cycloaliphatic alcohols having a carbon number of $C_1$–$C_{22}$, open-chain or cyclic.

N-vinylamides (vinyllactams) of a ring size of from 3 to 9, for example N-vinylformamide (VIFA), N-vinylmethylformamide, N-vinylmethylacetamide (VIMA), N-vinylacetamide, N-vinylpyrrolidone (NVP) and N-vinylcaprolactam. Amides of acrylic or methacrylic acid can also be used as monomers. Examples which may be mentioned are, inter alia, acrylamide, N,N-dimethylacrylamide, N,N-diethylacrylamide, methacrylamide, alkoxylated acrylamides or methacrylamides (for example MAPTAC, APTAC). Other suitable monomers are 2- and 4-vinylpyridine, vinyl acetate, glycidyl methacrylate, acrylonitrile, vinylphosphonic acid and esters or alkali metal, alkaline earth metal or ammonium salts thereof, DADMAC and vinylsulphonic acid or its corresponding $Na^+$, $K^+$, $Li^+$, $Mg^{2+}$ or $Ca^{2+}$ salts. It is, of course, also possible for combinations of the monomers listed to be present. As already mentioned, the sum of the comonomers used can be from 9.99 to 98.99% of the total mass of the polymer. The polymers used according to the invention as drift control agents in crop protection compositions can be crosslinked, i.e. they contain compounds having at least two double bonds which are polymerized into the polymer. Suitable crosslinkers are, in particular, methylenebisacrylamide or methylenebismethacrylamide, esters of unsaturated mono- or polycarboxylic acids of polyols, such as diacrylate or triacrylate or methacrylates, for example butanediol or ethylene glycol diacrylate or methacrylate, and also trimethylolpropane tri(meth)acrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and derivatives of vinylphosphonic acid, furthermore, allyl or vinyl ethers, for example dipropylene glycol diallyl ether, polyglycol diallyl ether, triethylene glycol divinyl ether, hydroquinone diallyl ether, multifunctional alcohols, tetraethylene glycol diacrylate, trimethylolpropane diallyl ether, methylene-bis-acrylamide or divinylbenzene.

The polymers according to the invention are prepared by free-radical copolymerization in $C_1$–$C_6$-alcohols, preferably in tert-butanol.

The polymerization can be carried out at in a temperature range of from 0 to 150° C., preferably between 10 and 100° C., and at atmospheric pressure or else under elevated or reduced pressure. As usual, the polymerization can also be carried out in an atmosphere of protective gas, preferably under nitrogen.

For initiating the polymerization, it is possible to use high-energy fields or the customary chemical polymerization initiators, for example organic or inorganic peroxides, such as benzoyl peroxide, tert-butyl hydroperoxide, methylene ketone peroxide, cumene hydroperoxide, azo compounds, such as, for example, azodiisobutyronitrile, and also inorganic peroxy compounds, such as $(NH_4)_2S_2O_8$ or $K_2S_2O_8$ or $H_2O_2$, if appropriate in combination with reducing agents, such as sodium hydrogen sulfite and iron(II) sulfate or redox systems which, as reducing component, comprise an aliphatic or aromatic sulfonic acid, such as benzenesulfonic acid and toluenesulfonic acid, or derivatives of these acids, such as, for example, Mannich adducts of sulfinic acid, aldehydes and amino compounds.

In general, the polymers have a number-average molecular weight of from 1000 to 20 000 000 g/mol. Preference is given to a molecular weight of from 20 000 to 5 000 000, in particular 100 000 to 1 500 000 g/mol.

The invention provides furthermore pesticide preparations comprising a copolymer of repetitive structural units of the formula (1), of structural units which are derived from olefinically unsaturated compounds containing an oxygen, nitrogen, sulfur or phosphorus atom and crosslinking structures as described above. These pesticide preparations may also comprise copolymers of the monomers of the formulae (2) and (3). In addition to these copolymers serving as drift control agents, the pesticide preparations comprise the customary active compounds, such as herbicides, insecticides, fungicides, acaricides, bactericides, molluscides, nematicides or rodenticides. Preference is given to herbicidal preparations. Suitable herbicidally active compounds are in particular glyphosate, but also acifluorfen, asulam, benazolin, bentazone, bilanafos, bromacil, bromoxynil, chloramben, clopyralid, 2,4-D, 2,4-DB, dalapon, dicamba, dichlorprop, diclofop, endothall, fenach, fenoxaprop, glamprop, fluazifop, flumiclorac, fluoroglacofen, fomesafen, fosamine, glufosinate, haloxyfop, imazapic, imazamethabenz, imazamox, imazapyr, imazaquin, imazethapyr, ioxynil, MCPA, MCPB, mecoprop, methylarsonic acid/MSMA, naptalam, picloram, quinclorac, quizalofop, 2,3,6-TBS-TCA.

The preparations according to the invention may comprise the copolymers based on acrylamidoalkylsulfonic acid salts as drift control agents in virtually any amount. Preference is given to the following preparations:

Formulations as tank-mix and ready-to-use compositions comprise from 0.01 to 10% by weight, preferably from 0.0025 to 2% by weight, of pesticide and from 0.0001% by weight to 5% by weight, preferably from 0.0025 to 2%, particularly preferably from 0.02 to 1%, of the copolymer according to the invention. The weight ratio of copolymer to pesticide can in this case be from 1:10 to 500:1, in particular from 1:4 to 4:1.

Concentrate formulations, which are diluted prior to use, may comprise the pesticide in amounts of from 5 to 60% by weight, preferably from 20 to 40%, and the copolymer based on acrylamidoalkylsulfonic acid salts in amounts of from 3 to 50% by weight. Here, the weight ratio of copolymer to pesticide can be from 1:20 to 1:1, preferably from 1:10 to 1:2.

In addition to the copolymers based on acrylamidoalkylsulfonic acid salts, the formulations according to the invention may comprise further thickeners, antigelling agents, antifreeze, solvents, dispersants, emulsifiers, preservatives, adjuvants, binders, antifoams, thinners and wetting agents.

The thinner used can be xanthan gum and/or cellulose, for example carboxy-, methyl-, ethyl- or propylcellulose, in amounts of from 0.01 to 5% by weight, based on the finished composition. Suitable solvents are monopropylene glycol and animal and mineral oils. Suitable dispersants and emulsifiers are nonionic, amphoteric, cationic and anionic surfactants.

Suitable for use as preservatives are organic acids and esters thereof, for example ascorbic acid, ascorbic acid palmitate, sorbate, benzoic acid, methyl- and propyl-4-hydroxybenzoate, propionate, phenol, for example 2-phenylphenate, 1,2-benzisothiazolin-3-one, formaldehyde, sulfurous acid and salts thereof. Suitable antifoams are polysilicones. Adjuvants that are available are polyglycerol esters, alcohol ethoxylates, alkylpolysaccharides, fatty amine ethoxylates, sorbitan and sorbitol ethoxylate derivatives and derivatives of alk(en) ylsuccinic anhydride. Suitable diluents, absorbents or carriers are carbon black, talc, kaolin, aluminum stearate, calcium stearate or magnesium stearate, sodium tripolyphosphate, sodium tetraborate, sodium sulfate, silicates and sodium benzoate.

The wetting agents used can be alcohol ethoxylates/ propoxylates.

To assess the effect of the copolymers used according to the invention, from the sodium salt of 2-acrylicamido-2-methylsulfonate and acrylamide, on the drift potential of an aqueous formulation, the mean droplet volumes of the spray mist and the distribution of the droplet size were determined both under normal conditions and under the action of shear forces and compared with the values determined for pure water.

TABLE 1

Mean diameter (μm) of the droplets

| Substance | Diameter (μm) Without shear forces | With shear forces |
|---|---|---|
| Water | 262 | 260 |
| Emigen DPR | 476.1 | 296.3 |
| Polymer 1 | 510 | 420 |

At a temperature of 20° C., an aqueous solution of 0.12 g/l of polymer 2000 or 12.00 g/l of Emigen DPR/I was sprayed using a Teejet XR8003 VS spray nozzle (tip@ 40 psi) from a distance of 30 cm on to an Aerometrics PDPA laser measuring system (325 volts), and the particle diameter of 10 000 droplets was determined. In each case, the measurement was carried out in three repetitions. Using a rotary pump at a rotation speed of 4.0 gal/min and a total of 12 rotations, the aqueous solutions were, at a temperature of 20° C., subjected to shear forces, and the droplet diameters were determined.

TABLE 2

Percentage of droplets < 150 μm, in % by volume

| Substance | % by volume Without shear forces | With shear forces |
|---|---|---|
| Water | 19.0 | 19.0 |
| Emigen DPR | 6.6 | 16.6 |
| Polymer 1 | 7.0 | 9.5 |

Chemical designation of Emigen ® DPR from Tables 1 and 2: Partially hydrolyzed polyacrylamide Polymer 1 was prepared as follows:

Copolymer of 70% by weight of AMPS and 30% by weight of AM, ammonium salt 1700 g of rectified tert-butanol were initially charged in a 3 liter Quickfit flask fitted with anchor stirrer, reflux condenser with waste-gas washer, combined thermometer/pH-meter and gas inlet tube, and admixed with 50 ml of distilled water. The reaction vessel was located in a thermostatted heating bath.

This reaction vessel was flashed with nitrogen gas, and in a gentle countercurrent of nitrogen, 245 g of acrylamido-2-methylpropanesulfonic acid AMPS 2404® (registered trade mark of Lubrizol) were introduced. The AMPS did not dissolve completely in the tert-butanol, and some of it was present as a solid-in-liquid dispersion. The pH of this mixture was below pH 1. Using the gas inlet tube, gaseous ammonia was introduced above the liquid phase until the pH of the dispersion was between pH 7 and 8. After the desired pH range had been reached, stirring was continued for 1 hour, and the pH was monitored continuously. The reaction vessel was once more flashed with nitrogen, and 105 g of acrylamide were introduced. After the acrylamide had been introduced, the pH was checked once more and, if required, adjusted to a range of pH 7–8. A constant stream of nitrogen was passed through the solution for at least 1 hour. After this inertization time, the residual oxygen content was checked using an oxygen electrode. If the measured residual oxygen content in the liquid phase is above the value of 1 ppm, the liquid phase has to be inertized again, until this value is reached. Subsequently 1.5 g of AIBN were added in a gentle stream of nitrogen, and the reaction vessel was heated to 60° C. Shortly after an internal temperature of 60° C. had been reached, introduction of nitrogen gas was terminated, the polymerization reaction typically starting after a few minutes, which could be detected by an increase in temperature of 10–15° C. Approximately 30 minutes after the polymerization reaction had started, the temperature maximum had been passed, and the temperature in the reaction vessel was increased to the boiling point of tert-butanol, using the heating bath.

Under gentle reflux, the material, which was now viscous, was stirred for another two hours.

The reaction product, present as a viscous suspension of polymers in tert-butanol, was separated off by filtering off the tert-butanol, followed by dying in a vacuum drying cabinet.

Yield: 365 g of polymer 1

Ammonium salt of poly (acrylamido-2-methylpropanesulfonic acid-co-acrylamide)

Dry matter: 96% by weight (2.5% by weight of tert-butanol, 1.5% by weight of water)

k-value of a 0.5% by weight strength solution: 212.

What is claimed is:

1. A pesticide preparation, comprising copolymers consisting essentially of from 1 to 90% by weight of the repetitive structural unit of the formula (1)

(1)

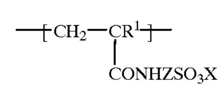

in which $R^2$ is hydrogen or methyl, Z is a $C_1$–$C_4$-alkylene group and X is hydrogen, an alkali metal or ammonium, from 10 to 99% by weight of a repetitive structural unit which is derived from olefinically unsaturated comonomers containing at least one oxygen, nitrogen, sulfur or phosphorus atom and from 0 to 20% by weight of crosslinking structures originating from monomers having at least two olefinic double bonds.

* * * * *